United States Patent
Cameron et al.

[11] Patent Number: 6,070,456
[45] Date of Patent: Jun. 6, 2000

[54] APPARATUS FOR EVALUATING FUEL LUBRICITY AT ELEVATED PRESSURE CONDITIONS

[75] Inventors: Alastair Cameron, Great Wilbraham, United Kingdom; David A. Cusac, East Peoria; Marcel R. Hanard, II, Dunlap, both of Ill.

[73] Assignee: Caterpillar Inc., Peoria, Ill.

[21] Appl. No.: 09/209,898

[22] Filed: Dec. 11, 1998

[51] Int. Cl.[7] .................................................. G01N 33/26
[52] U.S. Cl. .............................................. 73/53.05; 73/10
[58] Field of Search ............................ 73/53.05, 54.23, 73/54.28, 49.7, 10

[56] References Cited

U.S. PATENT DOCUMENTS

| | | | |
|---|---|---|---|
| 1,989,627 | 1/1935 | Sage | 175/183 |
| 2,019,948 | 11/1935 | Boerlage | 265/10 |
| 4,228,674 | 10/1980 | Mertway | 73/10 |

OTHER PUBLICATIONS

ISO/DIS 12156–1.3—Diesel Fule—Measurement of Lubricity by HFRR—Part 1: Test Method—Aug. 1996—9 pages.

*Primary Examiner*—Hezron Williams
*Assistant Examiner*—Thuy Vinh Tran
*Attorney, Agent, or Firm*—Kathleen M. Ryan

[57] ABSTRACT

Apparatus for evaluating fuel lubricity under elevated pressure conditions is disclosed. The apparatus includes a housing including a sidewall defining an enclosed interior cavity adapted for receiving and holding a quantity of the fuel at the elevated temperature and pressure condition, and a port through the sidewall communicating with the interior cavity adapted for receiving a drive rod. A drive rod is positioned to extend through the port, the drive rod having a working end including a chuck adapted for supporting a ball for oscillating movement in the interior cavity of the housing, and an opposite drive end located externally of the housing adapted for connection to a power source operable for moving the drive rod to oscillate the chuck and the ball along a predetermined path of movement in the interior cavity. A seal member extends around the drive rod forming a sealed condition between the drive rod and the housing. A load applying member is located in the interior cavity along the predetermined path of movement, and structure is provided operable for biasing the load applying member against the ball during the oscillating movement thereof.

14 Claims, 5 Drawing Sheets

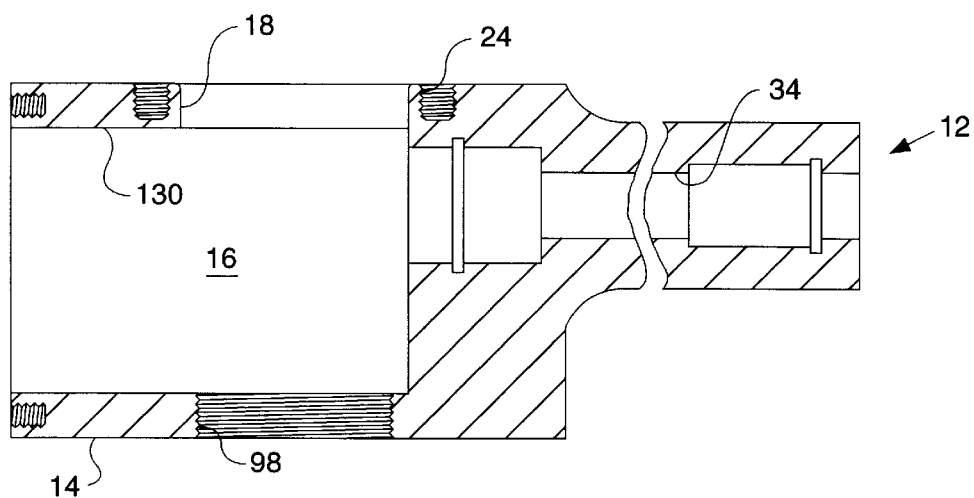
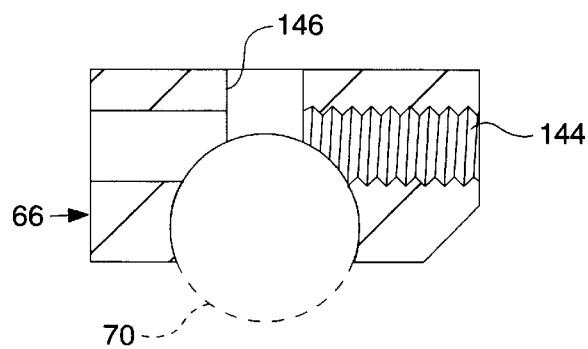
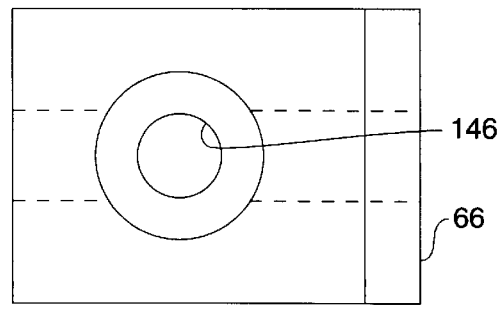

Fig. 4.
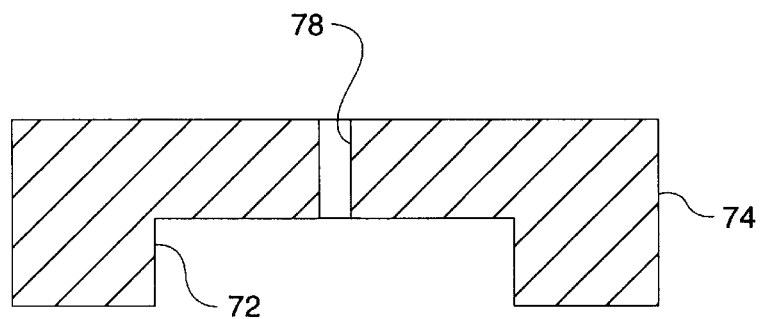
Fig. 5.
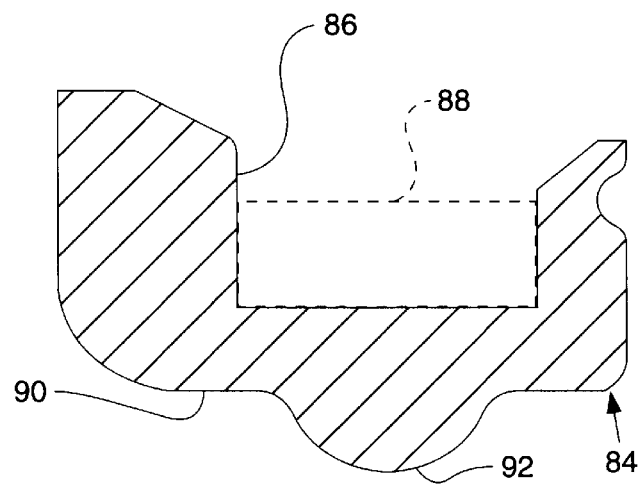
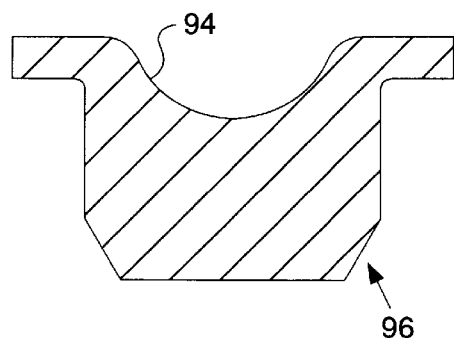

APPARATUS FOR EVALUATING FUEL LUBRICITY AT ELEVATED PRESSURE CONDITIONS

TECHNICAL FIELD

This invention relates generally to apparatus for evaluating fuel lubricity, and more particularly, to apparatus for evaluating fuel lubricity under elevated temperature and pressure conditions representative of actual operating conditions for the fuel.

BACKGROUND ART

Many fuel systems, particularly fuel injection systems, rely on the fuel as a lubricant for one or more components thereof. Wear due to friction has been found to shorten the life of many of the components, such as fuel injection pumps and injectors, because of inadequate fuel lubricity.

Currently, a widely used procedure for evaluating fuel lubricity is to place a sample of a fuel to be tested in a test reservoir at the ambient atmospheric pressure and a specified test temperature. A fixed steel ball is held in a vertically mounted chuck and forced against a horizontally mounted stationary steel plate or disk under an applied load. The test ball is oscillated at a fixed frequency and stroke length parallel to the surface of the plate or disk, while the interface with the plate is fully immersed in the fuel. The metallurgies of the ball and plate, load, frequency, and stroke length are specified. Then, the ambient conditions during the test are used to correct the size of a wear scar or flat generated on the test ball to a standard set of ambient conditions, and the corrected wear scar diameter is used as a measure of the lubricating properties of the fuel. The test parameters, such as stroke length, oscillation frequency, temperature, applied load, and duration are specified under international testing standards. See for instance, the ISO/DIS 12156-1.3 test standard for the measurement of the lubricity of diesel fuel.

However, in many internal combustion engines, the fuel is maintained at elevated pressures, that is, pressures much greater than ambient atmospheric pressure conditions, for instance, 150 psi and greater, such that fuel lubricity is an important operating factor when selecting a fuel. Further, it has been found that fuel lubricity values determined under ambient atmospheric pressure conditions do not necessarily serve as an accurate predictor of actual fuel lubricity at the elevated actual operating pressure conditions.

Accordingly, the present invention is directed to overcoming one or more of the problems as set forth above.

DISCLOSURE OF THE INVENTION

In one embodiment of the present invention apparatus for evaluating fuel lubricity under elevated pressure conditions is disclosed. The apparatus includes a housing including a sidewall defining an enclosed interior cavity adapted for receiving and holding a quantity of the fuel at the elevated pressure condition, and a port through the sidewall communicating with the interior cavity adapted for receiving a drive rod. A drive rod is positioned to extend through the port, the drive rod having a working end including a chuck adapted for supporting a ball for oscillating movement in the interior cavity of the housing, and an opposite drive end located externally of the housing adapted for connection to a power source operable for moving the drive rod to oscillate the chuck and the ball along a predetermined path of movement in the interior cavity. A seal member extends around the drive rod forming a sealed condition between the drive rod and the housing. A load applying member is located in the interior cavity along the predetermined path of movement, and structure is provided operable for biasing the load applying member against the ball during the oscillating movement thereof.

According to a preferred embodiment, the present apparatus is operable to evaluate fuel lubricity within a temperature range of at least between about 100° C. and about 150° C., and at a pressure between about 30 and 90 pounds per square inch (psi), which are representative of temperature and pressure operating conditions for a variety of internal combustion engine fuel systems.

BRIEF DESCRIPTION OF THE DRAWINGS

For a better understanding of the present invention, reference may be made to the accompanying drawings in which;

FIG. 2 is a cross sectional view of a housing of the apparatus of FIG. 1;

FIG. 3A is a cross sectional view of a ball chuck of the apparatus of FIG. 1;

FIG. 3B is a bottom view of the ball chuck of FIG. 3A;

FIG. 4 is an end view of a guide block of the apparatus of FIG. 1;

FIG. 5 is a cross sectional view of a test disk holder assembly of the apparatus of FIG. 1;

BEST MODE FOR CARRYING OUT THE INVENTION

Figure 1:
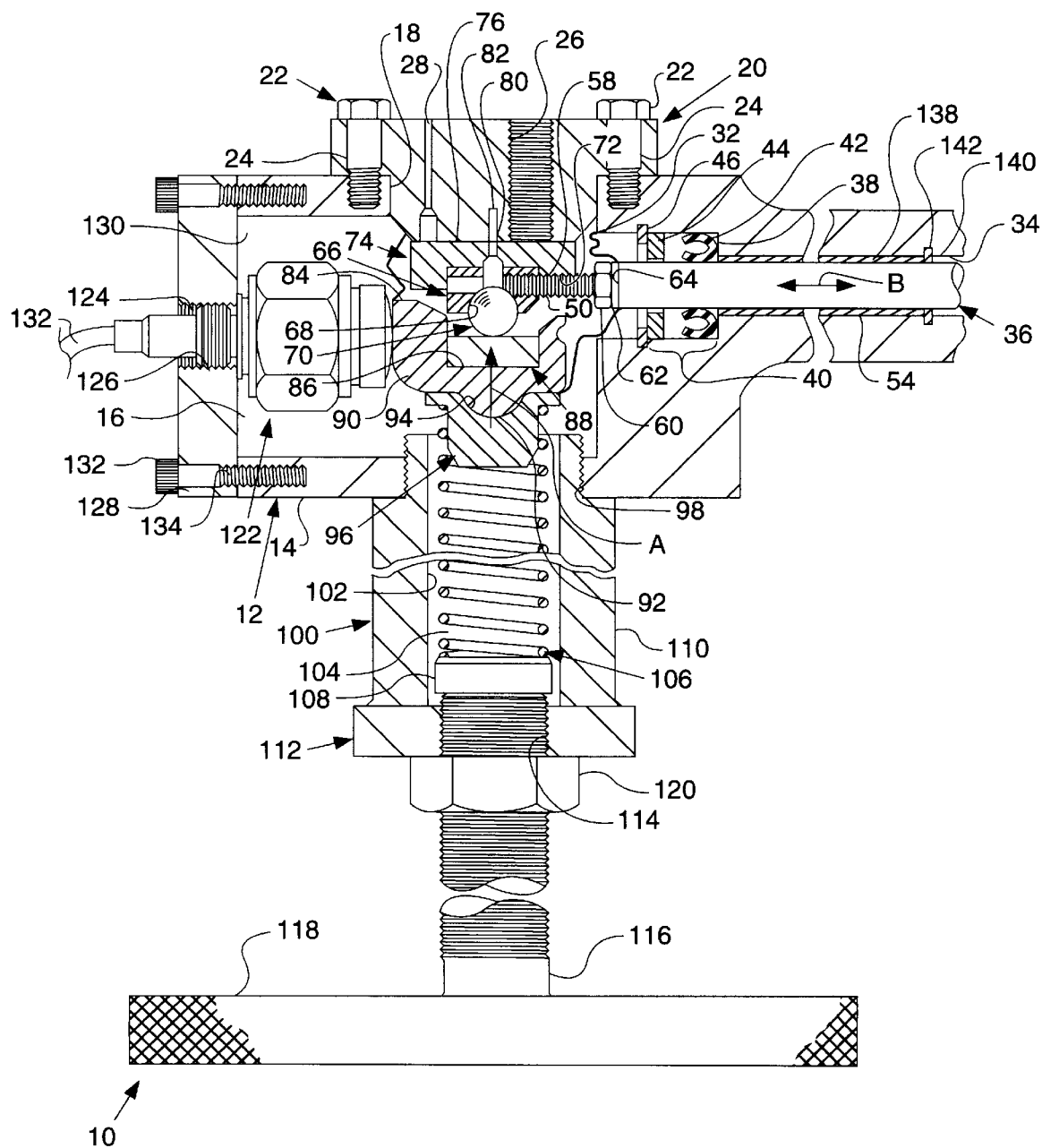
FIG. 1 is a side view in partial cross section of apparatus for evaluating fuel lubricity according to the present invention.

Referring now to the drawings, the numeral 10 in FIG. 1 identifies apparatus for evaluating fuel lubricity constructed and operable according to the teachings of the present invention. Apparatus 10 is operable to test fuel lubricity under elevated temperature and elevated pressure conditions simulative of actual operating conditions in an internal combustion engine or the like. In particular, apparatus 10 is adapted for the evaluation of the lubricity of fuels at a temperature range of between about 100° C. and about 240° C., and at elevated pressure conditions of as much as 90 psi and greater, which reflect actual temperature and pressure conditions in a variety of fuel injected internal combustion engines.

Apparatus 10 includes a metal housing 12 having a sidewall 14 which defines an enclosed interior cavity 16 adapted for pressurization at the elevated pressure conditions. Sidewall 14 includes a top opening 18 in communication with interior cavity 16, opening 18 being adapted for cooperatively receiving a top cap 20 in sealed relation thereto held in place using suitable structure or fasteners, such as a plurality of bolts 22 threadedly receivable in threaded apertures 24 located in housing 12 around top opening 18. Top cap 20 includes a threaded fuel inlet port 26 communicating with interior cavity 16 and adapted for threaded connection with a fuel line in communication with a source of fuel at the elevated pressure condition (not shown) for supplying a flow of the fuel to interior cavity 16 and for pressurizing interior cavity 16 at the elevated pressure condition. Additionally, top cap 20 includes an optional bleeder port 28 therethrough communicating with interior cavity 16 and adapted for flow of excess amounts of the fuel from interior cavity 16. An interior volume 32 is adapted for receiving and holding the fuel which enters the interior cavity 16 to contain and prevent dispersal of the fuel throughout the cavity. Housing 12 further includes a drive rod port 34 extending through sidewall 14 in communication with interior cavity 16, drive rod port 34 being adapted for receiving an elongated drive rod 36 for longitudinally oscillating movement therein, and an interior counterbore 38 extending around drive rod port 34 adapted for cooperatively receiving a seal assembly 40 for forming a sealed condition between drive rod 36 and sidewall 14. Seal assembly 40 can be of any suitable conventional construction such as the construction shown including an annular elastomeric seal member 42 of C-shaped cross section which extends around drive rod 36 and is held in position and protected by a similarly disposed seal ring 44 and an annular clip 46 located in an annular groove 48 extending around counterbore 38.

Drive rod 36 has a working end 50 located in interior cavity 16, an opposite drive end 52 (FIG. 7), and an intermediate portion 54 therebetween which passes through drive rod port 34 and is sealably engaged by seal assembly 40. Working end 50 includes a threaded end portion 58 which threadedly receives a nut 60 located in interior volume 32 tightenable against a washer 62 for forming a sealed condition with the drive rod 36. A ball chuck 66 is threadedly mounted to threaded end portion 58 of drive rod 36 in interior volume 32. Ball chuck 66 is moveable with drive rod 36 and includes a generally semi-spherical cavity 68 adapted for cooperatively receiving and holding a ball 70, as shown. When viewed from the top or bottom (FIG. 3B), ball chuck 66 has a rectangular shape and is adapted for cooperative sliding receipt in a rectangularly shaped channel 72 in a guide block 74 also located in interior volume 32. Guide block 74 has a generally planar top surface 76 and a centrally located hole 78 therein adapted for receiving one end of a locating pin 80, the opposite end of the locating pin being received in a hole 82 for positioning and holding guide block 74 in abutting relation to top cap 20 during the oscillating movement of ball chuck 66 relative thereto.

A test disk holder 84 is located in interior volume 32 along a path of oscillating movement of ball 70 and includes a disk shaped cavity 86 which is adapted for cooperatively receiving and holding a load applying member which is a test disk 88 in position for slidable contact with ball 70 during the oscillating movement thereof. Test disk holder 84 has an outer surface 90 adapted to be located in intimate contact with the lower portion of the interior volume 32, and a downwardly extending button 92 which is cooperatively receivable in a correspondingly shaped recess 94 in an upper spring retainer 96 located in interior cavity 16 of housing 12.

Apparatus 10 includes structure for resiliently biasing test disk 88 against ball 70 during the oscillation thereof, including a threaded aperture 98 in sidewall 14 adjacent upper spring retainer 96 adapted for sealably and threadedly receiving a threaded end of a cylindrical shaped metal spring housing 100. Spring housing 100 includes an inner sidewall 102 defining a cavity 104 in pressurized communication with interior cavity 16 of housing 12. Cavity 104 is adapted for cooperatively receiving a compression coil spring 106. Compression coil spring 106 has an upper end engaged with upper spring retainer 96 and a lower end engaged with a lower spring retainer 108 located in cavity 104. Spring housing 100 has a lower end 110 esalably enclosed by a metal flange 112 welded or otherwise mounted thereto. Flange 112 has a threaded aperture 114 therethrough which sealably and threadedly receives a threaded adjuster rod 116. Adjuster rod 116 extends into cavity 104 of spring housing 100 and abuts lower spring retainer 108. Adjuster rod 116 has a handle 118 affixed thereto to enable manually rotating the adjuster rod for changing the compression load on coil spring 106. A locking nut 120 is threadedly engaged with adjuster rod 116 and can be tightened against flange 112 when a desired compression loading of spring 106 is achieved. The compression loading of spring 106 operates to urge upper spring retainer 96 against test disk holder 84 holding test disk 88, which in turn urges or biases the test disk against ball 70 in a direction denoted by the arrow A, transverse to the direction of oscillating movement of ball 70 as denoted by the arrow B, to thus apply a desired load against ball 70. Other suitable load applying apparatus could likewise be used with similar utility.

A piezoelectric or similar force transducer 122 is located in interior cavity 16 of housing 12 in abutting relation with outer surface 90 of test disk holder 84. Force transducer 122 has an externally threaded connector 124 which is threadedly received in an internally threaded hole 126 through a metal end plate 128. End plate 128 is sealably mounted over a transducer opening 130 with a plurality of bolts 132 threadedly engaged in threaded holes 134 located at spaced locations around opening 130. Transducer 122 is of conventional construction and operation and further includes an electrically conductive wire 136 for communicating information representative of forces exerted thereagainst by test disk holder 84 to a data acquisition device (not shown) or other apparatus in the conventional manner. Drive rod port 34 of housing 12 can include optional structure facilitating the smooth oscillating movement of drive rod 36 therein, such as a Teflon brand self-lubricating guide bushing 138 shown, which is retained in position by a snap ring 140 located in an annular grove 142.

Briefly referring to FIG. 2, housing 12 is shown including sidewall 14 defining interior cavity 16, top opening 18, threaded apertures 24 for receiving bolts 22 (FIG. 1), drive rod port 34, threaded opening 98 and transducer opening 130.

Referring to FIGS. 3A and 3B, a side and bottom view respectively, of ball chuck 66 are shown. Ball chuck 66 has a threaded opening 144 adapted for threadedly receiving threaded end portion 58 of drive rod 36. Ball chuck 66 further includes a top opening 146 adapted for the insertion of a tool or pin (not shown) for ejecting ball 70 (in phantom) from cavity 68.

FIG. 4 is an end view of guide block 74 showing channel 72 therethrough for slidably receiving ball chuck 66, and hole 78.

Referring to FIG. 5, test disk holder 84 for holding test disk 88 (in phantom) and upper spring retainer 96 are shown. Cavity 86, outer surface 90 and button 92 are shown on the test disk holder, while recess 94 on spring retainer 96 is shown. Note that recess 94 is somewhat larger than button 92.

Figure 6:
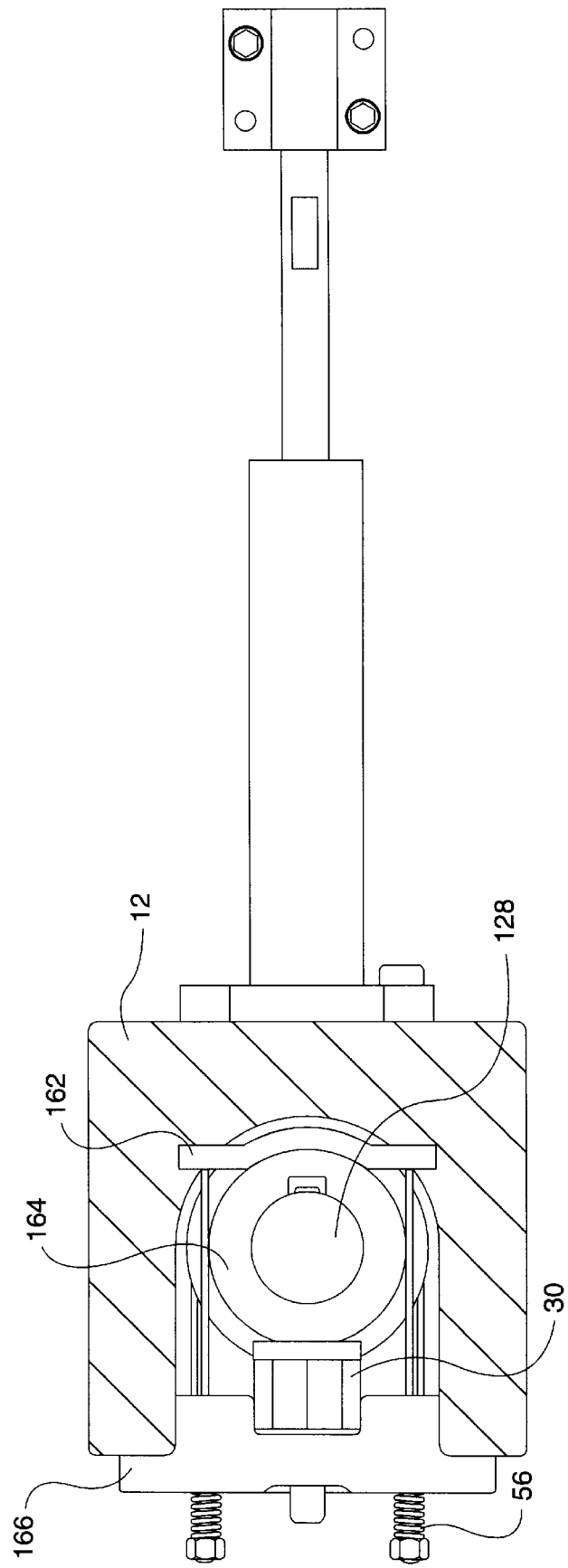
FIG. 6 is a top view of the apparatus of FIG. 1.

Turning to FIG. 6, a top view of the apparatus 10 is shown. The polarizing springs 56 are shown. The springs 56, must be axial to the piezo 30. Apparatus 10 also includes a metal housing 12 having a clamp 162 and a sleeve 164.

The sleeve 164 is affixed against the piezo 30 by the clamp 162 and four (4) bolts 168 through the rear cover 166. These four (4) bolts 168 have springs 56 which provide a tensile pull on the clamp 162. The polarizing springs 56 keep the sleeve 164 against the piezo 30 to provide accurate friction force measurement. The sleeve 164 allows for unbiased vertical translation of the test plate holder up to contact with the test ball. The housing 12 is the overall chamber which contains the test fluid at pressure and provides the positioning of the other operating components.

Figure 7:
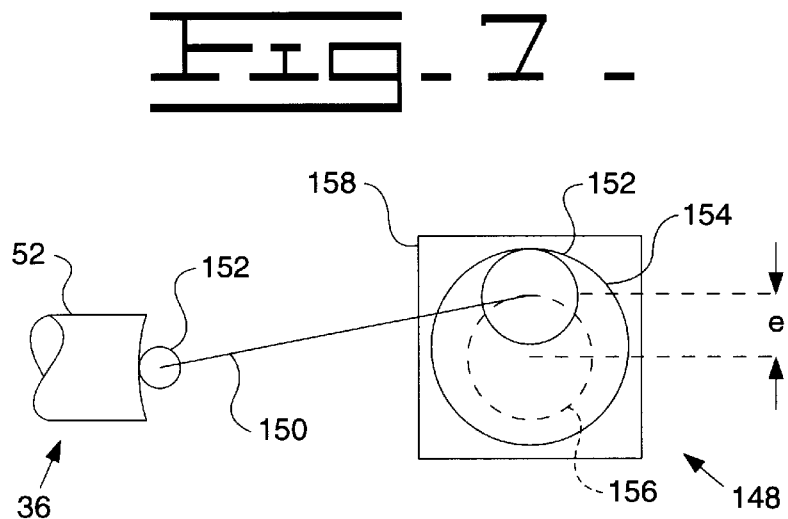
FIG. 7 is a schematic view showing one embodiment of drive apparatus for the apparatus of FIG. 1.

FIG. 7 is a schematic representation showing drive end 52 of drive rod 36, connected to one embodiment 148 of drive apparatus for longitudinally oscillating drive rod 36. Drive apparatus 148 includes a drive link 150 pivotally connected at one end by a pin 152 to drive end 52 of the drive rod 36 and pivotally connected at an opposite end to a crank bearing 154 mounted to an output shaft 156 of a drive motor 158 of conventional construction and operation. Drive link 150 is connected to crank bearing 154 at a location eccentric to output shaft 156 by a value denoted by the letter e, such that when drive motor 158 is operated to rotate output shaft 156, drive link 150 will longitudinally oscillate drive rod 36 in drive rod port 34 so as to likewise oscillate ball chuck 66 and ball 70 relative to test disk 88 (FIG. 1).

Other suitable drive apparatus could likewise be used with similar utility. As an alternative construction, fuel under pressure entering housing 12 through fuel inlet port 26 can be allowed to enter interior cavity 16 and cavity 104 directly. To allow testing of the fuel under dynamic conditions, the apparatus 10 can include a fuel outlet port 160 at any convenient and suitable location, such as through spring housing 100, as shown in FIG. 8.

Figure 8:
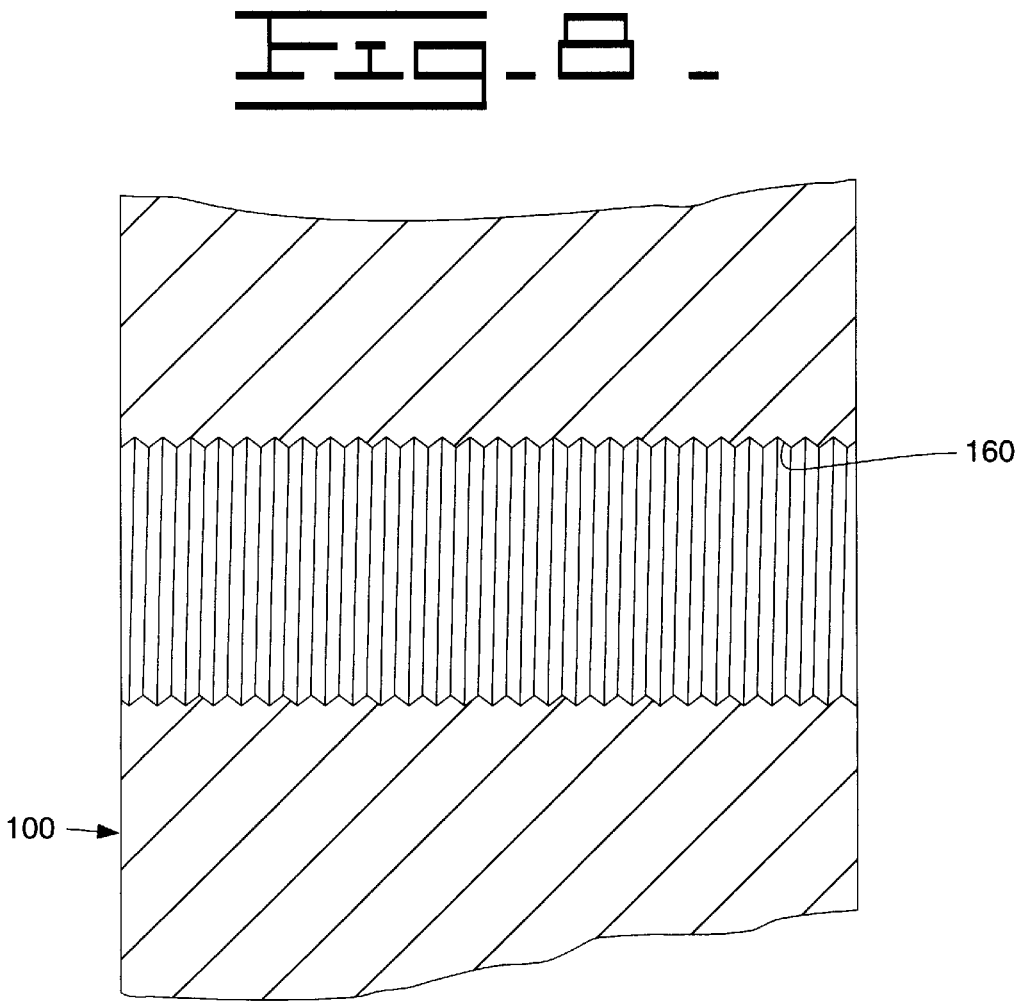
FIG. 8 is a fragmentary cross-sectional view of a spring housing of the apparatus of FIG. 1, showing an optional fuel outlet port therethrough.

Referring to FIG. 8 fuel outlet port 160 through spring housing 100 can be internally threaded as shown for threaded connection to a fuel return line or other conduit in communication with a receiver for the fuel (not shown).

In operation, oscillating movement of ball 70 with test disk 88 biased thereagainst under a predetermined load applied by spring 106 at the elevated pressure and temperature, will eventually produce a wear scar (not shown) on the ball. This wear scar can be evaluated and compared with regard to baseline wear scar data to determine the lubricity of the fuel contained by the apparatus 10.

INDUSTRIAL APPLICABILITY

The present apparatus for evaluating fuel lubricity at elevated pressure conditions is operable for evaluating lubricity of a wide variety of fuels at elevated temperature and pressure conditions of 90 pounds per square inch and greater, and at elevated temperature conditions, of from between about 100° C. and about 240° C., corresponding to actual operating conditions for a wide variety of internal combustion engines.

Other aspects, objects and advantages of the present invention can be obtained from a study of the drawings, the disclosure and the appended claims.

We claim:

1. An apparatus adapted for testing lubricity of a fuel at an elevated pressure condition, comprising:
    a housing including a sidewall defining an enclosed interior cavity adapted for receiving and holding a quantity of the fuel at the elevated pressure condition, and a port through the sidewall communicating with the interior cavity adapted for receiving a drive rod;
    a drive rod extending through the port, the drive rod having a working end including a chuck adapted for supporting a ball for oscillating movement in the interior cavity of the housing, and an opposite drive end located externally of the housing adapted for connection to a power source operable for moving the drive rod to oscillate the chuck and the ball along a predetermined path of movement in the interior cavity, a seal member extending around the drive rod forming a sealed condition between the drive rod and the housing;
    a load applying member located in the interior cavity along the predetermined path of movement, and structure operable for biasing the load applying member against the ball during the oscillating movement thereof; and
    a force transducer positioned for sensing forces acting against the load applying member during the oscillating movement of the ball.

2. Apparatus, as set forth in claim 1, wherein the structure operable for resiliently biasing the load applying member against the ball comprises a compression spring.

3. Apparatus, as set forth in claim 2, further comprising a mechanism allowing adjusting compression of the spring.

4. Apparatus, as set forth in claim 1, wherein the power source comprises an electric motor and an eccentric drive mechanism connected in driving communication with the drive end of the drive rod.

5. Apparatus, as set forth in claim 1, further comprising an interior cavity adapted for receiving and holding the fuel under pressure.

6. Apparatus, as set forth in claim 1, wherein the structure operable for resiliently biasing the load applying member against the ball comprises a handle allowing manual adjustment thereof.

7. Apparatus, as set forth in claim 1, wherein the housing is adapted for pressurization of the interior cavity thereof at a pressure of at least about 90 psi.

8. Apparatus adapted for testing lubricity of a fuel at an elevated pressure condition, comprising:
    a housing including a sidewall defining an enclosed interior cavity adapted for receiving and holding a quantity of the fuel at the elevated pressure condition, and a port through the sidewall communicating with the interior cavity adapted for receiving a drive rod, the housing being adapted for pressurization of the interior cavity thereof at a pressure of at least about 90 psi;
    a drive rod extending through the port, the drive rod having a working end including a chuck adapted for supporting a ball for oscillating movement in the interior cavity of the housing, and an opposite drive end located externally of the housing adapted for connection to a power source operable for moving the drive rod to oscillate the chuck and the ball along a predetermined path of movement in the interior cavity, a seal member extending around the drive rod forming a sealed condition between the drive rod and the housing; and
    a load applying member located in the interior cavity along the predetermined path of movement, and structure operable for biasing the load applying member against the ball during the oscillating movement thereof.

9. Apparatus, as set forth in claim 8, wherein the structure operable for resiliently biasing the load applying member against the ball comprises a compression spring.

10. Apparatus, as set forth in claim 9, further comprising a mechanism allowing adjusting compression of the spring.

11. Apparatus, as set forth in claim 8, further comprising a force transducer positioned for sensing forces acting against the load applying member during the oscillating movement of the ball.

12. Apparatus, as set forth in claim 8, wherein the power source comprises an electric motor and an eccentric drive mechanism connected in driving communication with the drive end of the drive rod.

13. Apparatus, as set forth in claim 8, further comprising an interior cavity adapted for receiving and holding the fuel under pressure.

14. Apparatus, as set forth in claim 8, wherein the structure operable for resiliently biasing the load applying member against the ball comprises a handle allowing manual adjustment thereof.

* * * * *

UNITED STATES PATENT AND TRADEMARK OFFICE
CERTIFICATE OF CORRECTION

PATENT NO. : 6,070,456
DATED : June 6, 1999
INVENTOR(S) : Alastair Cameron, et. al.

It is certified that error appears in the above-identified patent and that said Letters Patent is hereby corrected as shown below:

Please change the title to:

APPARATUS FOR EVALUATING FUEL LUBRICITY AT ELEVATED TEMPERATURE AND PRESSURE CONDITIONS

Signed and Sealed this

Twenty-second Day of May, 2001

Attest:

NICHOLAS P. GODICI

*Attesting Officer*     *Acting Director of the United States Patent and Trademark Office*